United States Patent [19]
Hatfield et al.

[11] Patent Number: 5,899,863
[45] Date of Patent: May 4, 1999

[54] METHOD AND APPARATUS FOR SEGMENTING B-MODE INTENSITY DATA USING DOPPLER SHIFT DATA IN THREE-DIMENSIONAL ULTRASOUND IMAGING

[75] Inventors: William Thomas Hatfield, Schenectady, N.Y.; Todd Michael Tillman, West Milwaukee; Patricia A. Schubert, Milwaukee, both of Wis.

[73] Assignee: General Electric Company, Milwaukee, Wis.

[21] Appl. No.: 08/852,259

[22] Filed: May 7, 1997

[51] Int. Cl.$^6$ ............................................. A61B 8/00
[52] U.S. Cl. ............................................. 600/443; 128/916
[58] Field of Search .................... 600/443, 447; 128/916

[56] References Cited

U.S. PATENT DOCUMENTS

| | | | |
|---|---|---|---|
| 5,226,113 | 7/1993 | Cline et al. | 395/124 |
| 5,329,929 | 7/1994 | Sato et al. | 128/916 |
| 5,365,929 | 11/1994 | Peterson | 128/661.1 |
| 5,474,073 | 12/1995 | Schwartz et al. | 128/661.1 |
| 5,485,842 | 1/1996 | Quistgaard | 128/660.07 |
| 5,497,776 | 3/1996 | Yamazaki et al. | 128/916 |
| 5,582,173 | 12/1996 | Li | 128/600.07 |
| 5,655,535 | 8/1997 | Friemel et al. | 128/660.07 |

FOREIGN PATENT DOCUMENTS

WO 97/00482  1/1997  WIPO .

Primary Examiner—Marvin M. Lateef
Assistant Examiner—Maulin Patel
Attorney, Agent, or Firm—Dennis M. Flaherty; Christian G. Cabou; Phyllis Y. Price

[57] ABSTRACT

A method and an apparatus for improving the segmentation of a three-dimensional B-mode image by limiting the volume of pixel intensity data projected onto the imaging planes. If the volume of interest contains moving ultrasound scatterers, e.g., blood flowing in an artery or vein, the Doppler shift present in the ultrasound reflected from the flowing blood can be detected and then used to limit the amount of pixel data which is projected. The velocity or power data is used to identify those intensity values to be projected onto the imaging plane. This is accomplished by locating a reference data volume of pixels for which the velocity or power value is non-zero and then defining a source data volume which is essentially a function of that reference data volume. The reference data volume comprises pixels acquired from echo return signals reflected by the moving ultrasound scatterers. The source data volume comprises both pixels acquired from echo return signals reflected by the blood flow and pixels acquired from echo return signals reflected by the artery or vein containing that blood flow. Pixels outside the source data volume are not used to reconstruct the projected images of the artery or vein.

26 Claims, 6 Drawing Sheets

METHOD AND APPARATUS FOR SEGMENTING B-MODE INTENSITY DATA USING DOPPLER SHIFT DATA IN THREE-DIMENSIONAL ULTRASOUND IMAGING

FIELD OF THE INVENTION

This invention generally relates to ultrasound imaging of the human anatomy for the purpose of medical diagnosis. In particular, the invention relates to a method for imaging the human anatomy by detecting the intensity of ultrasonic echoes reflected by a scanned volume in a human body.

BACKGROUND OF THE INVENTION

Conventional ultrasound scanners create two-dimensional B-mode images of tissue in which the brightness of a pixel is based on the intensity of the echo return. In color flow imaging, the movement of fluid (e.g., blood) or tissue can be imaged. Measurement of blood flow in the heart and vessels using the Doppler effect is well known. The frequency shift of backscattered ultrasound waves may be used to measure the velocity of the backscatterers from tissue or blood. The change or shift in backscattered frequency increases when blood flows toward the transducer and decreases when blood flows away from the transducer. The Doppler shift may be displayed using different colors to represent speed and direction of flow. In power Doppler imaging, the power contained in the returned Doppler signal is displayed. The color flow mode displays hundreds of adjacent sample volumes simultaneously, all color-coded to represent each sample volume's velocity. The color flow image may be superimposed on the B-mode image.

The present invention is incorporated in an ultrasound imaging system consisting of four main subsystems: a beamformer 2 (see FIG. 1), processor subsystem 4, a scan converter/display controller 6 and a master controller 8. System control is centered in master controller 8, which accepts operator inputs through an operator interface (not shown) and in turn controls the various subsystems. The master controller also generates the system timing and control signals which are distributed via a system control bus 10 and a scan control bus (not shown).

The main data path begins with the digitized RF inputs to the beamformer from the transducer. The beamformer outputs two summed digital baseband receive beams. The baseband data is input to B-mode processor 4A and color flow processor 4B, where it is processed according to the acquisition mode and output as processed acoustic vector (beam) data to the scan converter/display processor 6. The scan converter/display processor 6 accepts the processed acoustic data and outputs the video display signals for the image in a raster scan format to a color monitor 12. The scan converter/display controller 6, in cooperation with master controller 8, also formats multiple images for display, display annotation, graphics overlays and replay of cine loops and recorded timeline data.

The B-mode processor 4A converts the baseband data from the beamformer into a log-compressed version of the signal envelope. The B function images the time-varying amplitude of the envelope of the signal as a grey scale using an 8-bit output for each pixel. The envelope of a baseband signal is the magnitude of the vector which the baseband data represent.

The frequency of sound waves reflecting from the inside of blood vessels, heart cavities, etc. is shifted in proportion to the velocity of the blood cells: positively shifted for cells moving towards the transducer and negatively for those moving away. The color flow (CF) processor 4B is used to provide a real-time two-dimensional image of blood velocity in the imaging plane. The blood velocity is calculated by measuring the phase shift from firing to firing at a specific range gate. Instead of measuring the Doppler spectrum at one range gate in the image, mean blood velocity from multiple vector positions and multiple range gates along each vector are calculated, and a two-dimensional image is made from this information. The color flow processor produces velocity (8 bits), variance (turbulence) (4 bits) and power (8 bits) signals. The operator selects whether the velocity and variance or the power are out-put to the scan converter. The structure and operation of a color flow processor are disclosed in U.S. Pat. No. 5,524,629, the contents of which are incorporated by reference herein.

The acoustic line memories 14A and 14B of the scan converter/display controller 6 respectively accept processed digital data from processors 4A and 4B and perform the coordinate transformation of the color flow and B-mode data from polar coordinate (R-θ) sector format or Cartesian coordinate linear array to appropriately scaled Cartesian coordinate display pixel data stored in X-Y display memory 18. In the B-mode, intensity data is stored in X-Y display memory 18, each address storing three 8-bit pixels. Alternatively, in the color flow mode, data is stored in memory as follows: intensity data (8 bits), velocity or power data (8 bits) and variance (turbulence) data (4 bits).

A multiplicity of successive frames of color flow or B-mode data are stored in a cine memory 24 on a first-in, first out basis. The cine memory is like a circular image buffer that runs in the background, continually capturing image data that is displayed in real time to the user. When the user freezes the system, the user has the capability to view image data previously captured in cine memory. The graphics data for producing graphics overlays on the displayed image is generated and stored in the timeline/graphics processor and display memory 20. The video processor 22 multiplexes between the graphics data, image data, and timeline data to generate the final video output in a raster scan format on video monitor 12. Additionally it provides for various greyscale and color maps as well as combining the greyscale and color images.

The conventional ultrasound imaging system collects B-mode or color flow mode images in cine memory 24 on a continuous basis. The cine memory 24 provides resident digital image storage for single image review and multiple image loop review and various control functions. The region of interest displayed during single-image cine replay is that used during the image's acquisition. The cine memory also acts as a buffer for transfer of images to digital archival devices via the master controller 8.

Two-dimensional ultrasound images are often hard to interpret due to the inability of the observer to visualize the two-dimensional representation of the anatomy being scanned. However, if the ultrasound probe is swept over an area of interest and two-dimensional images are accumulated to form a three-dimensional volume, the anatomy becomes much easier to visualize for both the trained and untrained observer.

In three-dimensional ultrasound imaging of B-mode intensity data, the intensity data is difficult to segment due to poor contrast as well as the presence of noise and speckle in the data. However, if the region of interest can be limited, segmentation of the three-dimensional B-mode image could be improved.

SUMMARY OF THE INVENTION

The present invention is a method and an apparatus for improving the segmentation of a three-dimensional B-mode image by limiting the volume of pixel intensity data projected onto the imaging planes. If the volume of interest contains flowing blood, i.e., an artery or vein, the Doppler shift present in the ultrasound reflected from the flowing blood can be detected and then used to limit the amount of pixel data which is to be projected onto various imaging planes for three-dimensional imaging of the artery or vein.

The apparatus incorporating the invention comprises an ultrasound scanner which collects color flow mode images in a cine memory on a continuous basis or in response to an external trigger event, i.e., for a multiplicity of slices. In the color flow mode, each pixel comprises an 8-bit intensity value derived from the amplitude of an echo return signal from a particular sample volume and an 8-bit velocity or power value derived from any Doppler shift detected in the same echo return signal from the same sample volume.

In accordance with the method of the present invention, the velocity or power data is used to identify those B-mode intensity values which are to be projected by a master controller onto an imaging plane. This is accomplished by locating a reference data volume of pixels for which the velocity or power value is greater than a minimum threshold or less than a maximum threshold or both. In accordance with one preferred embodiment, the pixels in the reference data volume are determined by those velocity or power values which are non-zero. The reference data volume is then used to define a source data volume for use in reconstructing projected images. The reference data volume corresponds to an object volume containing moving ultrasound scatterers, e.g., flowing blood in an artery or vein. Having defined a reference data volume corresponding to blood flow, it is a relatively straightforward matter to further define a source data volume containing the reference data volume and approximately corresponding to an object volume encompassing at least the artery or vein through which the detected blood flow is flowing.

In accordance with one preferred embodiment, the source data volume can be formed by, first, determining an object volume which is a circular cylinder having a centerline and a predetermined radius corresponding to one-half the dimension defined by successive pixels having a non-zero velocity or power component, and then increasing the radius of that same circular cylinder by a sufficient amount to define a larger object volume encompassing the artery or vein. The dimensions of the source data volume are then set equal to the dimensions of the larger object volume. The pixels inside the source data volume are used in reconstructing the projections onto various imaging planes. Pixels outside the source data volume are not used to reconstruct those projections. The result is a projected B-mode image having improved segmentation. Thus, by using the B-mode intensity data from only those pixels in a volume of interest which either have a velocity or power component or are within a predetermined distance of pixels having a velocity or power component, extraneous information is eliminated and the resulting B-mode projection is greatly improved.

The master controller performs an algorithm that projects the pixel intensity data in the volume of interest onto a plurality of rotated image planes using a ray-casting technique. The projected intensity data resulting from each projection is then stored in the cine memory, optionally superimposed on unprojected intensity data from the last frame read from the X-Y memory prior to freezing of the system by the operator. The intensity data is stored in cine memory such that when the intensity data is displayed, the projected intensity data will be superimposed on a central region of the displayed frame, with unprojected intensity data displayed on the frame perimeter. These reconstructed frames stored in cine memory can then be displayed selectively by the system operator.

DETAILED DESCRIPTION OF THE PREFERRED EMBODIMENTS

Figure 1:
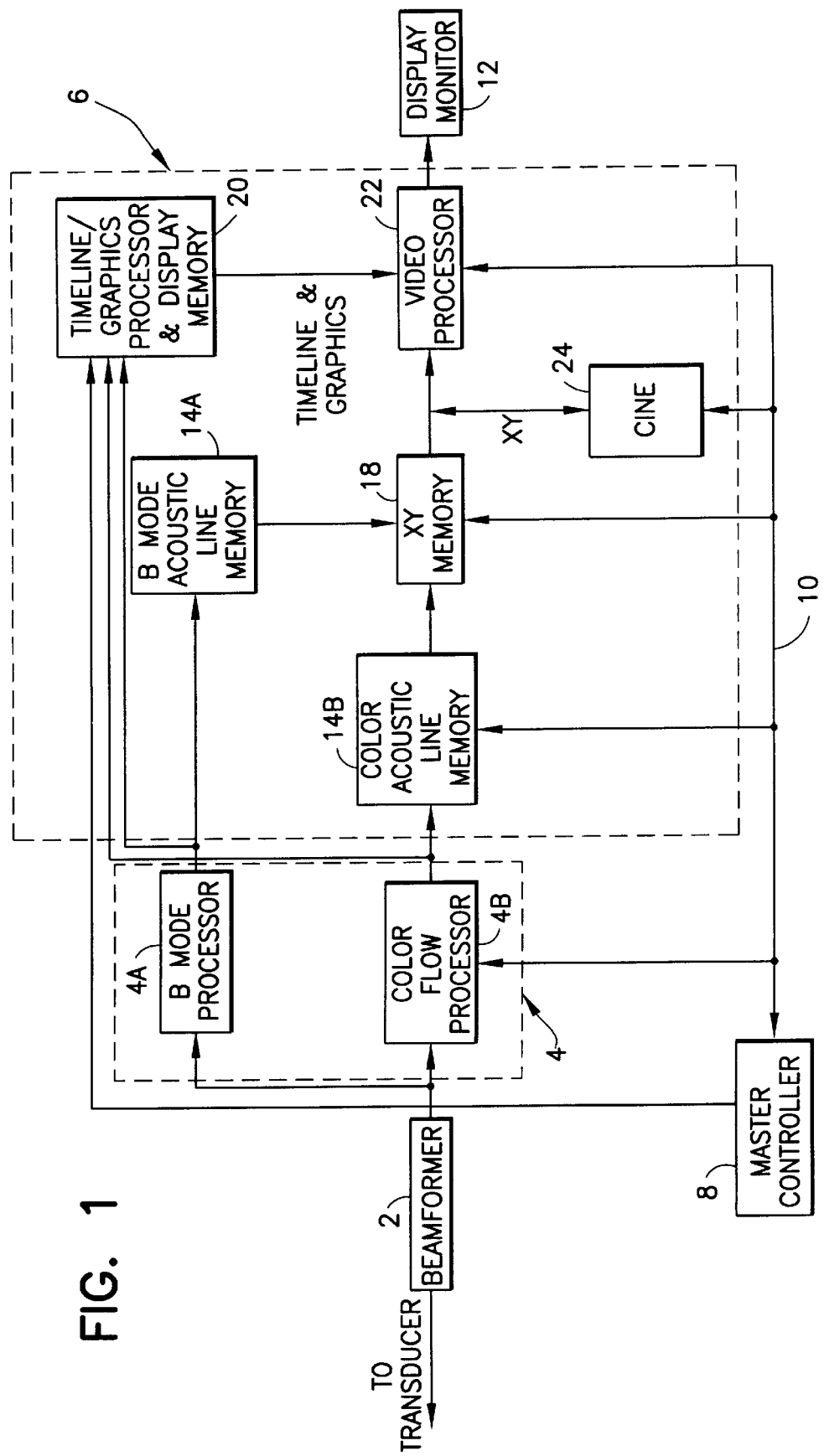
FIG. 1 is a block diagram showing the major functional subsystems within a real-time ultrasound imaging system.
Figure 2:
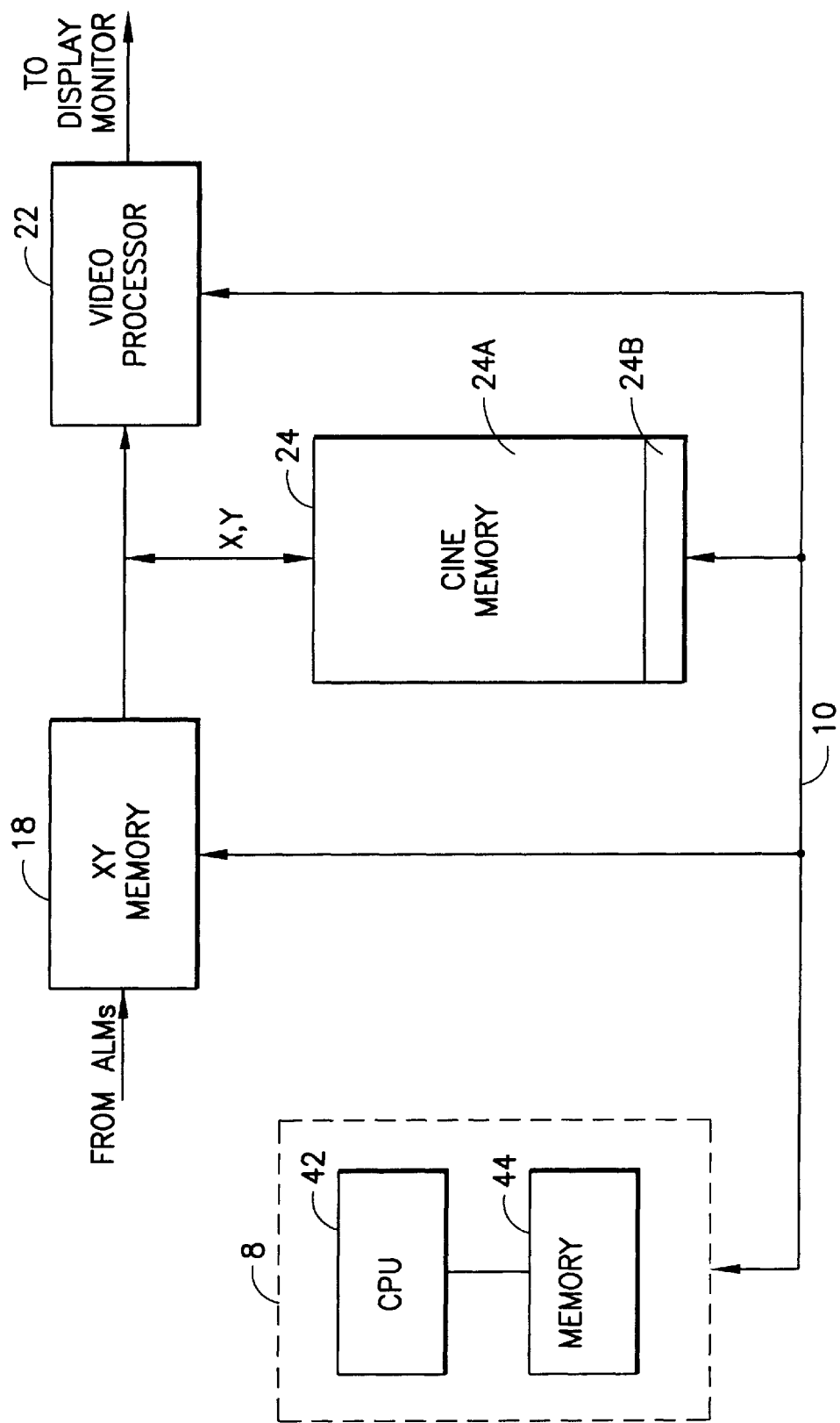
FIG. 2 is a block diagram showing the means for reconstructing frames comprising successive volumetric projections of pixel intensity data in accordance with the invention.

Referring to FIG. 2, the master controller 8 comprises a central processing unit (CPU) 42 and a random access memory 44. The CPU 42 has read only memory incorporated therein for storing routines used in transforming the acquired volume of intensity and velocity or power data into a multiplicity of three-dimensional projection images taken at different angles. The CPU 42 controls the XY memory 18 and the cine memory 24 via the system control bus 10. In particular, the CPU 42 controls the flow of data from the XY memory 18 to the video processor 22 and to the cine memory 24, and from the cine memory to the video processor 22 and to the CPU 42 itself. When the ultrasound imaging system is operating in the color flow mode, each frame of color flow data, representing one of a multiplicity of scans or slices through the object being examined, is stored in the XY memory 18 and in the next cycle is transmitted to video processor 22 and to cine memory 24. A stack of frames, representing the scanned object volume, is stored in section 24A of cine memory 24. During initialization (see step 26 in FIG. 3), the CPU 42 retrieves from cine memory section 24A only the color flow data corresponding to an object volume of interest. This is accomplished by retrieving only the color flow data in a region of interest from each stored frame acquired from any scan which intersected the object volume of interest. In other words, the color flow data corresponding to the region of interest from each one of a stack of successive frames forms a source data volume of interest.

Figures 3, 3A:
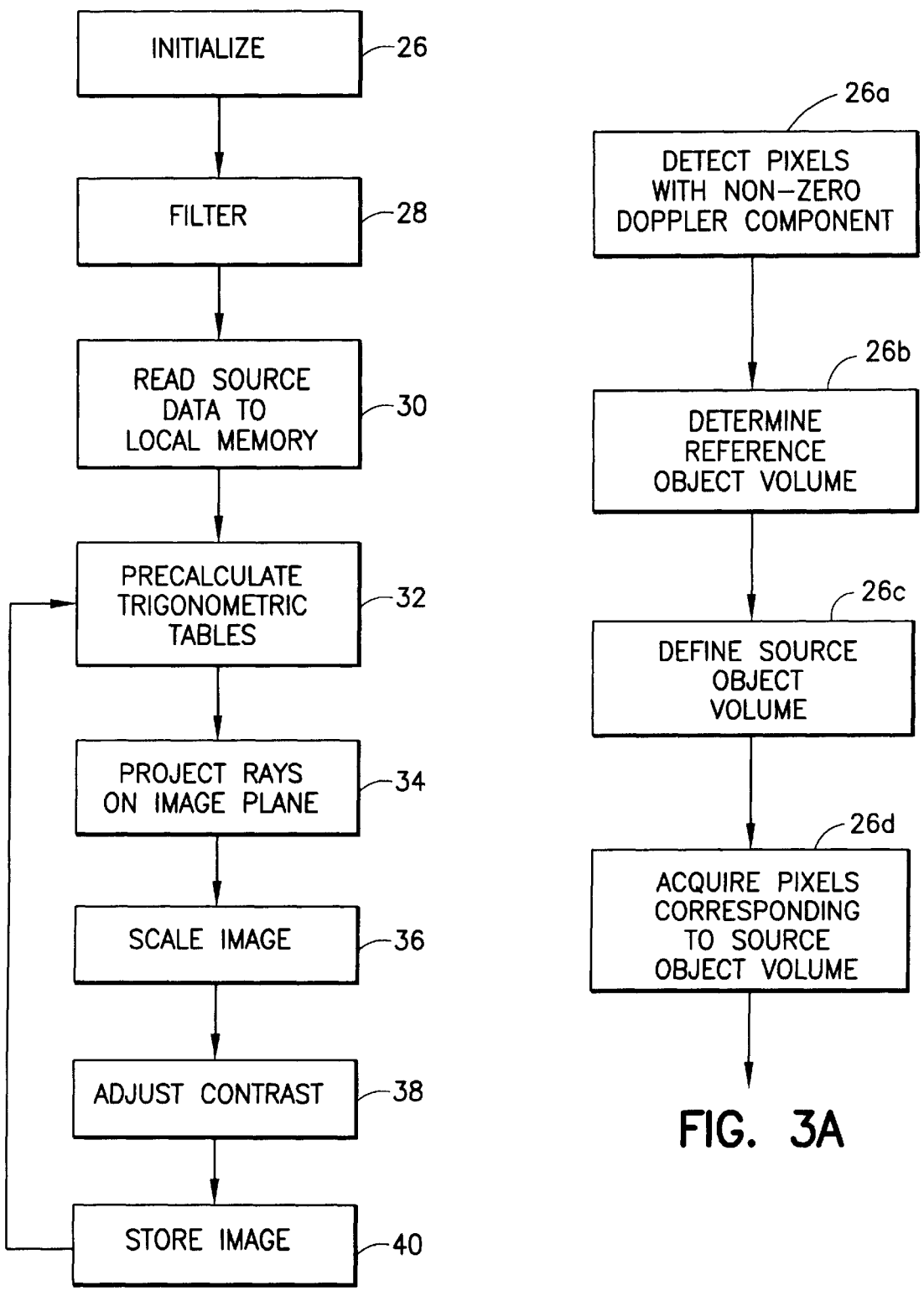
FIG. 3 is a flowchart showing the steps of an algorithm for reconstructing frames comprising successive volumetric projections of pixel intensity data in accordance with the invention.
FIG. 3A is a flowchart showing the steps involved in initialization in accordance with the preferred embodiment of the invention.

The initialization step is shown in greater detail in FIG. 3A. In accordance with the preferred embodiment of the invention, the source data volume of interest is a function of a reference data volume defined by those pixels in the volume of interest having a non-zero velocity or power component (step 26a). The reference data volume corresponds to a first object volume containing moving ultrasound scatterers, e.g., flowing blood in an artery or vein. In step 26b, the first object volume is approximated by a circular cylinder having a centerline and a first radius determined by one-half the number of consecutive pixels with non-zero velocity or power component lying along the diameter of that cylinder. The first radius should be approximately equal to the internal radius of the artery or vein. In step 26c, a second object volume is defined in terms of the first object volume in such a manner that the former encompasses the artery or vein surrounding the latter. In the preferred embodiment, the second object volume is defined by a circular cylinder having a centerline which is coaxial with the centerline of the first object volume and which has a second radius which is greater than the first radius by at least the thickness of the wall of the artery or vein being imaged. The source data volume of interest is then formed (step 26d in FIG. 3A) by retrieving from the cine memory the intensity data for only those pixels which were acquired from echo return signals reflected by sample volumes lying within the first object volume. Necessarily, the source data volume comprises those pixels acquired from echo return signals reflected from flowing blood inside the artery or vein (i.e., pixels having a non-zero velocity or power component) as well as those pixels acquired from echo return signals reflected from the artery or vein itself.

In accordance with the preferred embodiment of the invention, the source data volume is formed by determining a region of interest for each slice having a frame of data stored in cine memory. Each region of interest corresponds to the intersection of the respective slice with the second object volume. For each slice, the master controller retrieves only those pixels acquired from echo return signals reflected by sample volumes lying within the region of interest. The totality of acquired pixels forms the source data volume which is used to reconstruct projected images of the portion of the artery or vein lying inside the second object volume of interest. Pixels outside the source data volume are not used to reconstruct those projected images. The result is a projected B-mode image having improved segmentation.

Referring again to FIG. 3, the intensity data in the source data volume, i.e., the pixel data set corresponding to the second object volume, is optionally filtered (step 28) prior to projection in order to smooth speckle noise and reduce artifacts. This prevents the loss of data due to speckle noise during projection. For example, blood vessels are less echogenic than the surrounding tissue. Therefore vessels can be imaged using minimum intensity projections. Alternatively, in the reverse video/minimum mode, the intensity data is inverted to make the vessels bright instead of dark. The vessels can then be imaged using maximum intensity projections. To prevent the selection of maximum intensities which are bright speckle as opposed to desired pixel data, a filter can be used to remove such bright speckle intensities prior to projection.

The source data volume retrieved from the cine memory 24 (see FIG. 2) can be filtered by CPU 42 using, e.g., a 3×3 convolution filter having a 111 141 111 kernel, i.e., the central pixel of intensity data in each 3×3 pixel array in each slice or frame is replaced by an intensity value proportional to the sum of four times the value of the central pixel plus the sum of the values of the eight pixels surrounding that pixel. The filtered source data volume is then stored in memory 44 (step 30). In a similar manner, a convolution filter can be used to remove black holes in an image prior to minimum intensity projection.

Next the CPU 42 performs a series of transformations using the ray casting algorithm disclosed in U.S. Pat. No. 5,226,113. The successive transformations represent maximum, minimum or averaged intensity, velocity or power projections made at angular increments, e.g., at 10° intervals, within a range of angles, e.g., +90° to −90°. However, the angular increment need not be 10°; nor is the invention limited to any particular range of angles.

Figure 4:
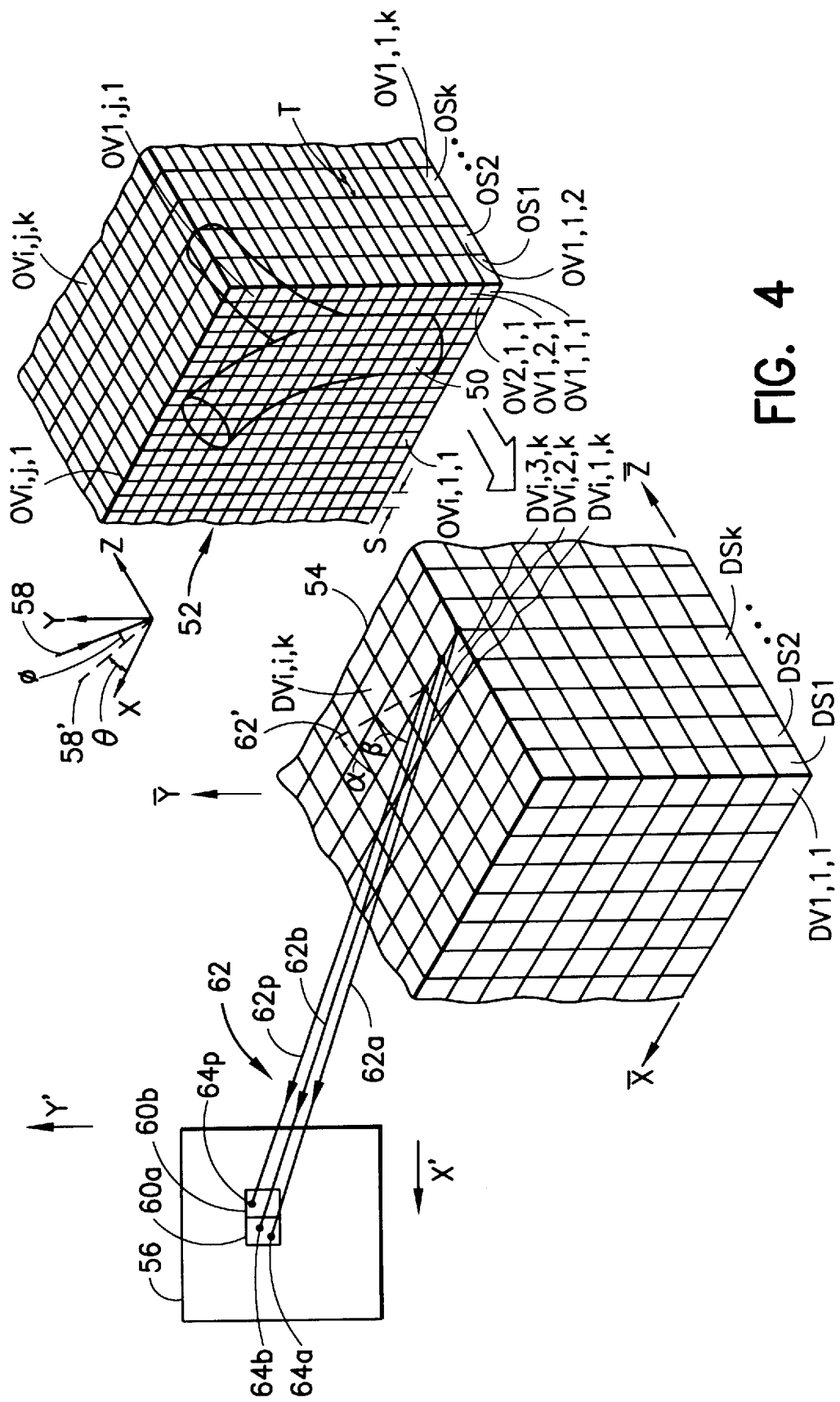
FIG. 4 is a schematic of the sampled object volume of interest, an associated data volume and an image projection plane involved in volumetrically rendering a reversed raycast projection in accordance with the prior art.

In accordance with the ray casting technique employed in the present invention, a volumetrically rendered projection image of a sample 50 (see FIG. 4) is displayed from any arbitrary viewing angle, e.g. a spherical projection angle denoted by angle parameters $(\theta,\phi)$, where $\theta$ is the angle that an extension 58' of a viewing ray 58 makes upon the X-Y plane, and $\theta$ is the angle of ray 58 with respect to extension 58', by scanning an object volume 52 using an ultrasound transducer. Sample volume 52 is scanned in such a manner as to create a series of stacked, contiguous slices or sheets $OS_1, OS_2, \ldots, OS_k$ each of which contains the same number of object volume elements (voxels) OV. Each voxel has a rectangular profile in the sheet plane (say, the X-Y plane); while the complementary sides may be of equal length S, so that this profile may be square, the sheet thickness T is generally not equal to the length of either side. Thus, the first object slice $OS_1$ contains a first multiplicity of object voxels $OV_{i,j,1}$, where i and j are the respective X-axis and Y-axis positions of the voxel. Similarly, the second object slice $OS_2$ contains object voxels $OV_{i,j,2}$. An arbitrary object slice $OS_k$ contains voxels $OV_{i,j,k}$, where k is the Z-axis position of that voxel.

Each object voxel $OV_{i,j,k}$ is analyzed and the data value (intensity, velocity or power) thereof is placed in a corresponding data voxel $DV_{i,j,k}$ of a data volume 54. Data volume 54 is a simple cubic i,j,k lattice, even though the thickness of each object slice $OS_k$ and each object voxel face size (the size of the voxel in the X-Y plane) will generally not be the same. That is, not only may the object volume have different X, Y and Z dimensions for each voxel, but also the total number of voxels in any dimension need not be the same. For example, a typical ultrasound three-dimensional scan may provide each slice with a 256×256 matrix of voxels, and may involve 128 slices.

In accordance with a known technique employed by CPU 42, an image of object 50 is projected (step 34 in FIG. 3) by ray casting toward the image plane 56 from a lattice point in data voxel $DV_{i,j,k}$. For convenience, the lattice point may, for example, be the data voxel vertex closest to the data volume origin. The cast ray 62 leaves the data volume 54 at a projection angle with spherical angular parameters $(\alpha,\beta)$ transformed from the spherical angular parameters $(\theta,\phi)$ at which the object volume 52 is viewed. These two angles are not the same, due to the geometric distortion caused by use of a cubic data volume 54 with a non-cubic object volume 52. However, the projected ray 62 has an $\overline{X}$-$\overline{Y}$ plane extension 62' which makes an angle $\alpha$ with respect to the $\overline{X}$ axis of the data volume, and ray 62 makes an angle $\beta$ with the Z axis. Thus, angles $\alpha$ and $\beta$ are determined by a rotation process (to be discussed hereinbelow) to correspond to viewing the object volume 52 at the desired viewing angle $(\theta,\phi)$ (assuming operation in spherical coordinates). Each of the rays 62 is cast from the data volume voxel lattice point toward the image plane.

While all rays 62 impinge upon some portion of the image plane, only those rays falling within the image plane pixel 60a under consideration are allowed to contribute to the data for that image plane pixel. Thus, having chosen a portion of the object volume 52 to view and a viewing angle $(\theta,\phi)$ at which to view this selected object volume, the data value in each voxel of the corresponding portion of the data volume is cast at some angle $(\alpha,\beta)$ (corresponding to viewing the distorted data volume with respect to the object volume) toward the image plane 56. The data value in a first voxel (say, voxel $DV_{i,1,k}$) is thus back-projected along ray 62a, in accordance with the $\theta$ and $\phi$ values chosen. This ray 62a impinges upon image plane 56 at a position 64a within pixel 60a, and, as this is the first ray to impinge upon this pixel, the intensity, velocity or power value of the incident data is attributed to (stored in) the desired pixel 60a. The next voxel in the data volume (say voxel $DV_{i,2,k}$) has its associated ray 62b projected at the same angular $(\alpha,\beta)$ configuration from the voxel lattice point, and its position 64b upon image plane 56 is noted. Assuming that impingement position 64b is within desired pixel 60a, the second projected value is (for a maximum pixel projection) compared with the now stored first value and the larger value is placed in storage for pixel 60a. It will be understood that, for an averaged-value projection, the value of a current projected data voxel is added to the sum already stored for the image panel pixel upon which that projection ray impinges, and the sum is eventually divided by a counted number of such impinging rays for that pixel. As each voxel in the selected data volume is sequentially entered and projected toward image plane 56, a data volume voxel (say, voxel $DV_{i,3,k}$) is eventually projected along its associated ray 62p and does not impinge within the desired pixel 60a, so that its data value (e.g., intensity) is not compared to the data value presently stored for pixel 60a. The maximum data value for pixel 60a is now established, for that projection of the data at the particular $(\theta,\phi)$ three-dimensional angle of view. However, the ray 62p does, in fact, have an impingement point 64p which falls within another image plane pixel (say, pixel 60b) and is compared to the data value stored therein and the larger value is, after the comparison, returned to storage for that pixel. All data values are reset to zero when a new projection is to be taken. Thus, each of the image plane pixels is reset at the start of an image projection procedure, and all of the data volume voxels (in the entire space or in the selected portion, as set by the portion of the object volume 52 selected) are individually and sequentially scanned. The data value in each data voxel DV is projected through an associated ray 62 to impinge upon image plane 56 in one pixel 60 thereof, with the maximum value in each pixel being compared between the present value of the ray-casted data volume voxel, to determine the larger thereof, which larger value is then stored as part of the maximum value image. In practice, for a maximum pixel projection, the stored maximum value will be changed only if the newly cast data voxel value is greater than the data value already stored for the image plane pixel upon which the newly cast ray impinges.

Figure 5:
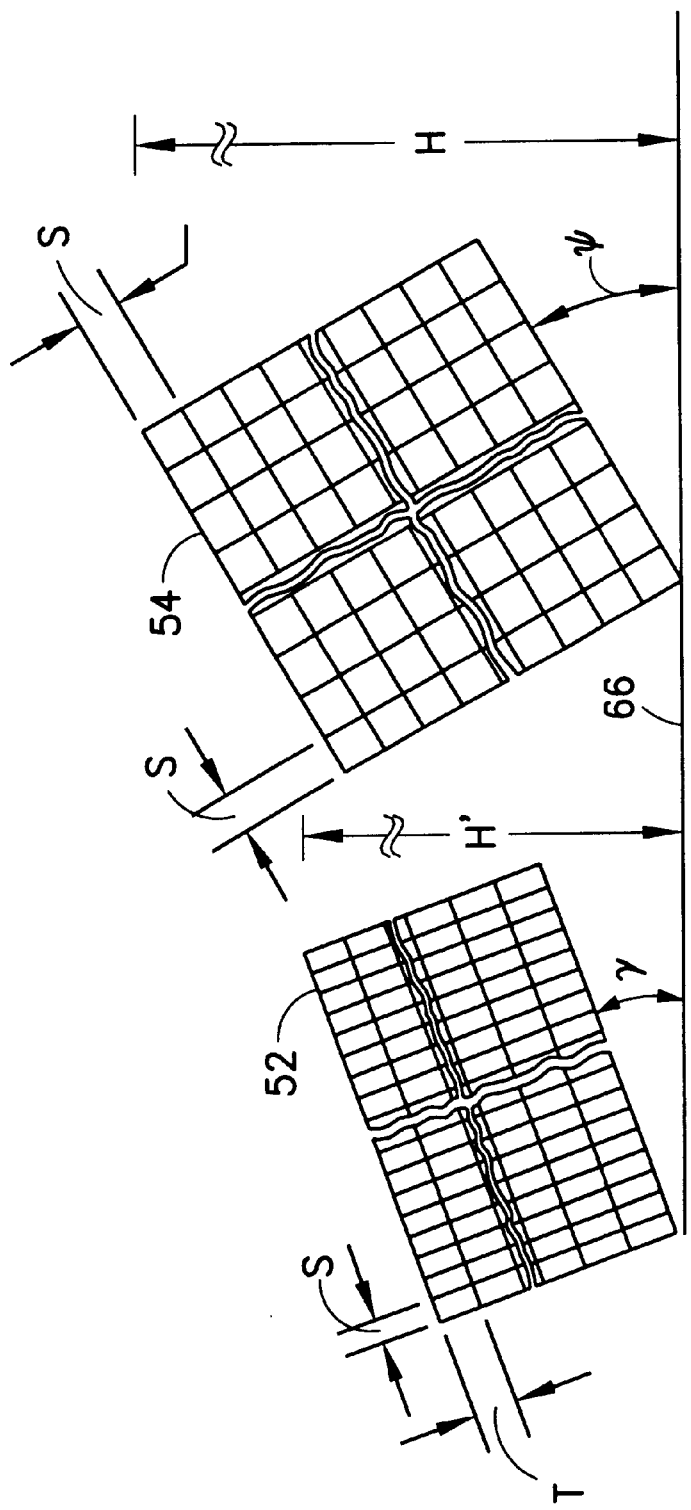
FIG. 5 is a schematic showing a pair of geometric two-dimensional configurations corresponding to like views of object and data volumes, and useful in defining necessary scaling constants in three-dimensional ultrasound imaging.

In accordance with another aspect of the foregoing technique, the data projection is scaled (step 36 in FIG. 3) and any anisotropy between the object volume and the image plane is removed by only a single set of calculations after back projection is complete. Referring now to FIG. 5, because object volume 52 is a real volume while data volume 54 is an abstract concept, it is necessary to determine the amount of distortion of the data projection due to the presentation of the cubic data volume lattice 54 at a different angle $\gamma$, in a first plane, then the angle $\psi$ at which an arbitrary viewing direction 66 will be positioned with respect to both the object volume 52 and data volume 54. The apparent dimensions of each voxel are going to change as the effective elevation angles $\psi$ and $\gamma$ change. If the aspect ratio A (defined as the ratio of the actual slice thickness T in object volume 52 to the actual pixel size S in the same object volume 52) is not unity (i.e., is greater or less than unity, as the object voxel is not a cubic voxel, as will be encountered in data volume 54), then the angles $\psi$ and $\gamma$ of elevation will be different, and the effective elevation angle $\psi$ in the data volume will be different than the actual elevation angle $\gamma$ in the object volume. Rotation of the data is in accordance with an object elevation angle obtained by:

$$\psi = \tan^{-1}\left(\frac{1}{A}\tan[\gamma]\right)$$

Thereafter, the projected data can be scaled to have the correct height (if rotation is about the horizontal axis) in the object volume, by multiplication of all projected data heights by the elevation scale factor. The old projected image height H can be corrected with an effective scale factor $E_s$, where $$E_s = \sqrt{(A\cos\gamma)^2 + \sin^2\gamma}$$

and the new height $H'=H.E_s$. The same is true for the width when rotation is about the vertical axis.

Utilizing the above relationship, the rotation of data volume angles $(\alpha,\beta)$ becomes angles $(\theta,\phi)$, because the distortion is only along one axis, so that angle $\theta$ equals angle $\alpha$. The elements of the 3×3 rotational matrix [M] can be determined, and given the two involved rotational angles, these relationships are used to determine the data volume-to-image plane transformations:

$$X'=M1X+M2Y+M3Z+XO$$

$$Y'=M4X+M5Y+M6Z+YO$$

where M1–M6 are the first two rows of the rotational matrix (i.e., M1=−sin $\theta$, M2=cos $\theta$ sin $\psi$, M3=0, M4=−cos $\theta$ sin $\psi$2, M5=−sin $\theta$ sin $\psi$, and M6=cos $\psi$), X' and Y' are the locations on the image plane of the projected point, and XO and YO are image plane X and Y offsets (respectively referenced to the X and Y lowest value points) at which the selected portion of the image plane begins. After the data is projected onto image plane 56, the image is scaled to correct for the effect of the anisotropic object voxels. It will be seen that factors M1–M6 can be precalculated (step 32 in FIG. 3) at the beginning of a projection (given $\theta$ and $\phi$) and used for all rotation calculations.

Figure 6:
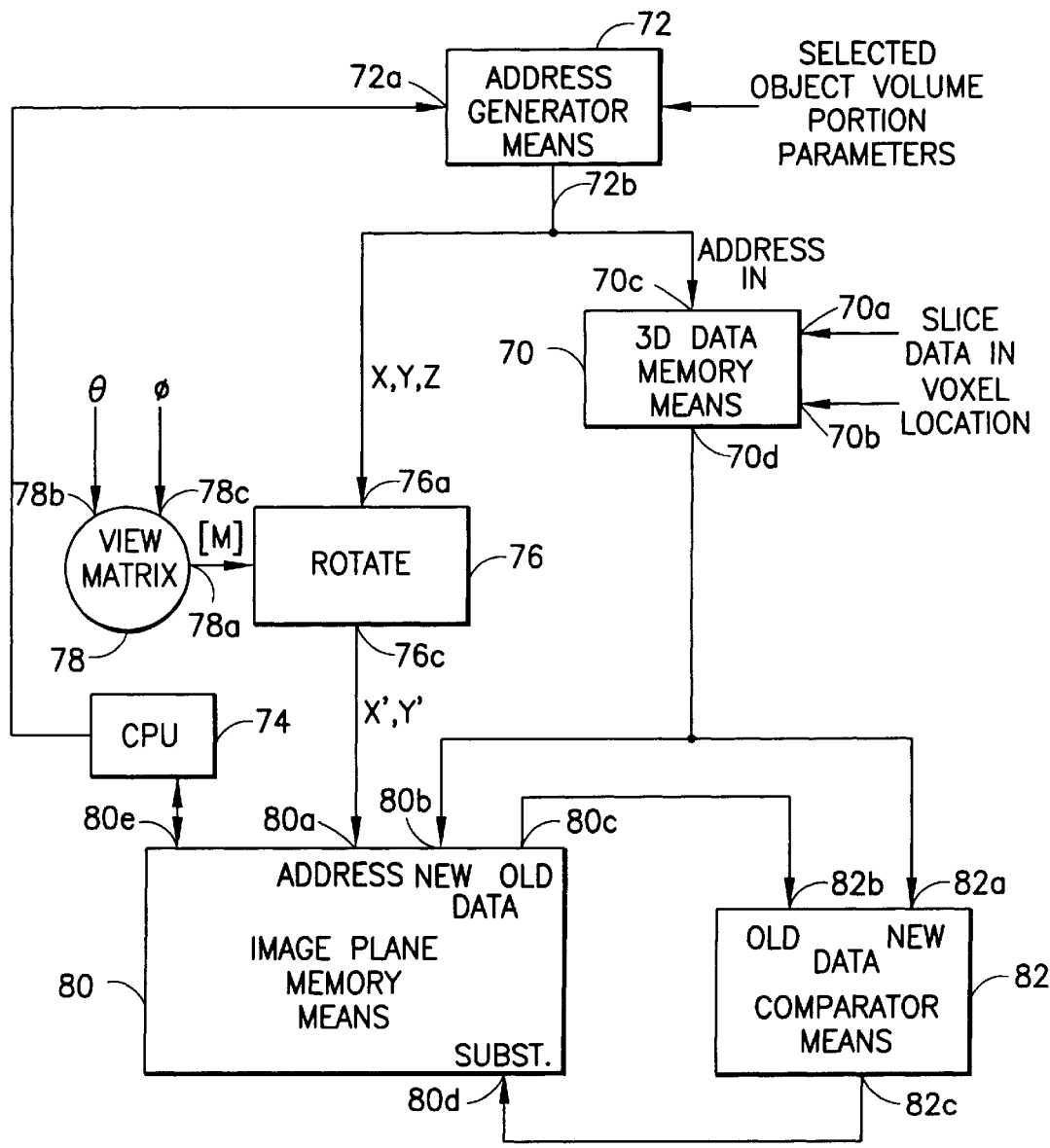
FIG. 6 is a schematic block diagram of means for providing a maximum intensity projection in three-dimensional ultrasound imaging.

FIG. 6 shows means for performing the above-described ray-casting technique which are incorporated in the master controller 8 (or a separate dedicated processor). Such means comprise a three-dimensional data memory means 70 for storing slice data as received at a data input 70a from cine memory 24. The data associated with each object voxel is stored at the address of that voxel, responsive to voxel address input information received at a voxel address input 70b from a CPU 74. Once the data memory means is filled (corresponding to the transfer of all required data from object volume 52 to data volume 54), the object volume portion of interest is selected and data establishing its starting corner and extent in the X, Y and Z directions is sent from CPU 74 to an input 72a of an address generator means 72. Means 72 sequentially provides, at an address output 72b, the X,Y,Z addresses of each voxel within the object volume selected. Output 72b is connected to an output-data-address input 70c of data memory means 70, causing the stored intensity data for that one voxel then addressed to be output from data memory means output 70d. The sequence of voxel X,Y,Z addresses is also provided to a first input 76a of a rotational parameter calculation means 76, which receives angle $(\alpha,\beta)$ information via CPU 74 as the calculated matrix element M1–M6 values, to provide at an output 76c the address X',Y' of the image plane pixel corresponding to that object X,Y,Z pixel when viewed at a selected viewing angle (θ,φ). The viewing angle (θ,φ) information is entered into the system and processed by CPU 74. The results are entered into inputs 78b and 78c of a viewing matrix means 78, to provide matrix elements M1–M6 at its output 78a and thence to rotational parameter calculation means 76. The image plane pixel address X', Y' appears at an address input 80a of a frame buffer acting as an image plane memory means 80. Simultaneously, the intensity data, projected from the data volume to the projection plane, appears at the image plane memory means new data input 80b, from three-dimensional data memory means output 70d. This data also appears at the new data input 82a of a data comparator means 82. Intensity data previously saved in the image plane memory means 80 for that address, at input 80a, appears at an old data output 80c, and thence at an old data input 82b of the comparator means. The old and new data at inputs 82b/82a, respectively, are compared in means 82 and an output 82c thereof is enabled to a selected logic condition (e.g., a high logic level) if the new data at input 82a has greater amplitude than the old data at input 82b. Output 82c is connected to a substitute-control data input 80d of the image plane memory means, to cause the data stored at the address controlled by input 80a to be changed to accept the new data at input 80b, if the substitute-data control input 80d is at the selected logic level. Thus, the stored data is initially reset, as by a signal through a data/control port 80e (from CPU 74), and the data of greatest value is stored for each image plane pixel location X',Y' responsive to a comparison indicating that the new data exceeds the value of the previously stored old data. After all of the selected addresses are sequentially scanned by address generator 72, the data stored in image plane memory means 80 is scaled in CPU 74, and the scaled image plane data can be withdrawn from memory means 80 for display, permanent storage or similar purposes.

In accordance with a further aspect of the invention, prior to display the scaled image plane data is mapped to achieve a desired brightness and contrast range (step 38 in FIG. 3). While reading in the region of interest for the source frames on which the three-dimensional reconstruction is based, a histogram of the number of pixels with a given intensity is optionally created in the master controller 8. Alternatively, the histogram can be formed using the projected images. At the same time, the maximum pixel intensity is determined. The pixels in each bin are counted until a given percentage of the total number of pixels is reached. This bin number becomes the pixel threshold. A map is then created such that each pixel value is mapped to the desired brightness and contrast range above or below the pixel threshold depending on the intended result.

The method shown in FIG. 3 is applied to the intensity data for the source data volume of interest retrieved from the cine memory. Each pixel in the projected image includes the transformed intensity data derived by projection onto a given image plane. In addition, at the time when the cine memory was frozen by the operator, the CPU 42 optionally stores the last frame from the XY memory 18 at multiple successive addresses in section 24B of cine memory 24. The projected image data for the first projected view angle is written into the first address in cine memory section 24B, so that the projected image data in a region of interest is superimposed on the background frame. This process is repeated for each angular increment until all projected images are stored in cine memory section 24B, each projected image frame consisting of a region of interest containing transformed intensity data and optionally a background perimeter surrounding the region of interest consisting of background intensity data not overwritten by the transformed intensity data. The background image makes it clearer where each displayed projection is being viewed from. The operator can then select any one of the projected images for display. In addition, the sequence of projected images can be replayed on the display monitor to depict the object volume as if it were rotating in front of the viewer.

The method of the invention is not limited with regard to the geometry of the source object volume. Although a circular cylindrical source object volume is preferable when imaging an artery or vein, it should be appreciated that other geometries can be used. The fundamental concept of the invention encompasses the formulation of a source object volume geometry which is a function of the object volume in which moving ultrasound scatterers are present.

Furthermore, although a preferred embodiment has been disclosed in which B-mode intensity data is projected when the associated flow velocity or power value is non-zero, it will be appreciated that the invention is not limited to acquisition of pixel data when the magnitude of the velocity or power component is not equal to zero. For some applications, the acquisition of B-mode intensity data can be gated by detecting only those velocity or power values which lie above a minimum threshold or below a maximum threshold or both. For example, velocities greater than zero but less than a predetermined threshold value can be detected in order to define a reference data volume corresponding to the blood flow in a boundary layer adjacent the wall of a vessel.

The ultrasound imaging system described above has a plurality of different projection modes. For example, the projection may include maximum or minimum value pixels. Alternatively, a mode useful in imaging blood vessels may be selected wherein the pixel data is inverted and then the maximum values are projected onto the image plane. In accordance with a further mode, the ray-casting technique can be employed to provide a surface rendering.

The foregoing preferred embodiment has been disclosed for the purpose of illustration. Variations and modifications of the basic concept of the invention will be readily apparent to those skilled in the arts of ultrasound imaging or computer graphics. All such variations and modifications are intended to be encompassed by the claims set forth hereinafter.

We claim:

1. A system for three-dimensional imaging of an object volume containing moving ultrasound scatters and tissue, comprising:

an ultrasound transducer array for transmitting ultrasound beams and detecting ultrasound echoes reflected from said object volume at a multiplicity of sample volumes;

means for acquiring Doppler data derived at least in part from ultrasound echoes reflected by the moving ultrasound scatters, each Doppler datum corresponding to a respective one of said multiplicity of sample volumes;

means for acquiring intensity data derived at least in part from ultrasound echoes reflected by the tissue, each intensity datum corresponding to a respective one of said multiplicity of sample volumes;

memory means for storing pixel data for each of said multiplicity of sample volumes, each pixel datum comprising a respective Doppler datum and a respective intensity datum corresponding to a respective sample volume;

means for determining a reference set of the pixel data stored in said memory means, said reference pixel data set consisting only of pixel data having a Doppler datum lying in a predetermined range;

means for retrieving a source set of the pixel data from said memory means to form a pixel data volume, the pixels included in said source pixel data set being a function of the pixels included in said reference pixel data set;

means for volumetrically rendering the intensity data in said source pixel data set by projecting onto a first image plane, thereby forming a volume projected data set representing a first projected image;

a display monitor; and means for displaying said first projected image on said display monitor.

2. The system as defined in claim 1, wherein the pixels included in said source pixel data set were derived from echo return signals reflected from sample volumes of said object volume, and said object volume has a dimension which is greater than a corresponding dimension determined from said reference pixel data set.

3. The system as defined in claim 2, wherein said object volume is a circular cylinder and said source dimension is a radius of said circular cylinder.

4. The system as defined in claim 1, wherein said Doppler data comprises velocity data.

5. The system as defined in claim 1, wherein said Doppler data comprises power data.

6. The system as defined in claim 1, further comprising:

means for projecting the intensity data in said source pixel data set onto a second image plane which is rotated relative to said first image plane, thereby forming a projected data set representing a second projected image; and means for displaying said second projected image on said display monitor.

7. A method for three-dimensional imaging of an object volume containing moving ultrasound scatters and tissue, comprising the steps of:

transmitting ultrasound beams into said object volume;

detecting ultrasound echoes reflected from said object volume at a multiplicity of sample volumes;

acquiring Doppler data derived at least in part from ultrasound echoes reflected by the moving ultrasound scatters, each Doppler datum corresponding to a respective one of said multiplicity of sample volumes;

acquiring intensity data derived at least in part from ultrasound echoes reflected by the tissue, each intensity datum corresponding to a respective one of said multiplicity of sample volumes;

storing pixel data for each of said multiplicity of sample volumes, each pixel datum comprising a respective Doppler datum and a respective intensity datum corresponding to a respective sample volume;

determining a reference set of the stored pixel data, said reference pixel data set consisting only of pixel data having a Doppler datum lying in a predetermined range;

retrieving a source set of the pixel data from the stored pixel data to form a pixel data volume, the pixels included in said pixel data volume being a function of the pixels included in said reference pixel data set;

volumetrically rendering the intensity data in said source pixel data set by projecting onto a first image plane, thereby forming a volume projected data set representing a first projected image; and displaying said first projected image.

8. The method as defined in claim 7, wherein the pixels included in said source pixel data set were derived from echo return signals reflected from sample volumes of said object volume, and said object volume has a dimension greater than a corresponding dimension determined from said reference pixel data set.

9. The method as defined in claim 8, wherein said object volume is a circular cylinder and said source dimension is a radius of said circular cylinder.

10. The method as defined in claim 7, wherein said retrieving step comprises the following steps:

determining a centerline and a first dimension of a first object volume formed by said multiplicity of sample volumes containing said moving ultrasound scatterers;

determining a thickness of tissue adjacent said moving ultrasound scatterers;

defining a second object volume having said centerline and a second dimension equal to at least the sum of said first dimension and said thickness; and forming said source pixel data set by retrieving the pixel data derived from echo return signals reflected by sample volumes within said second object volume.

11. The method as defined in claim 10, wherein said first and second object volumes are concentric circular cylinders having first and second radii respectively, said first dimension being equal to said first radius and said second dimension being equal to said second radius.

12. The method as defined in claim 7, wherein said Doppler data comprises velocity data.

13. The method as defined in claim 7, wherein said Doppler data comprises power data.

14. The method as defined in claim 7, further comprising the steps of:

projecting the intensity data in said source pixel data set onto a second image plane which is rotated relative to said first image plane, thereby forming a projected data set representing a second projected image; and displaying said second projected image.

15. A method for three-dimensional imaging of an object volume containing a moving ultrasound scatterers bounded by tissue, comprising the steps of:

transmitting ultrasound beams into said object volume;

detecting ultrasound echoes reflected from said object volume at a multiplicity of sample volumes;

processing the ultrasound echo from each sample volume to acquire a respective Doppler datum;

processing the ultrasound echo from each sample volume to acquire a respective intensity datum;

correlating said Doppler data with said intensity data to form a respective pixel datum for each sample volume, said pixel data comprising a first set of pixel data having a Doppler component above a predetermined threshold value and a second set of pixel data having a Doppler component below said predetermined threshold value, said second pixel data set being limited to pixel data acquired from sample volumes within a first object volume having a predetermined relationship to a second object volume formed by sample volumes containing the moving ultrasound scatterers, said predetermined relationship being a function of the configuration of the tissue bounding the moving ultrasound scatterers;

acquiring a source set of intensity data, said source intensity data set including at least intensity data taken from said second set of pixel data;

volumetrically rendering said source set of intensity data by protecting onto a first image plane to form a first projected image of tissue; and displaying said first projected image of tissue.

16. The method as defined in claim 15, wherein said first and second object volumes are concentric circular cylinders having first and second radii respectively, said first radius being greater than said second radius.

17. The method as defined in claim 15, wherein said Doppler data comprises velocity data.

18. The method as defined in claim 15, wherein said Doppler data comprises power data.

19. The method as defined in claim 15, further comprising the steps of:

projecting said source set of intensity data onto a second image plane which is rotated relative to said first image plane to form a second projected image of tissue; and displaying said second projected image of tissue.

20. The method as defined in claim 15, wherein said source intensity data set does not include intensity data derived from sample volumes located outside said first object volume.

21. An imaging system comprising:

an ultrasound transducer array comprising a multiplicity of transducer elements;

a transmit beamformer programmed to cause said transducer array to transmit in sequence a plurality of focused beams which scan a plane;

a receive beamformer programmed to form respective beamsummed receive signals from respective sets of signals transduced by said transducer array following transmission of said respective beams;

a Doppler data processor programmed to derive a set of Doppler data from said beamsummed receive signals;

a B-mode data processor programmed to derive a set of intensity data from said beamsummed receive signals;

a memory for storing said sets of Doppler and intensity data in the form of sets of pixel data, each pixel datum comprising a Doppler datum and an intensity datum derived from ultrasound scattered from a particular sample volume; an image data processor programmed to perform the steps of:

(a) determining a reference set of the pixel data stored in said memory, said reference pixel data set consisting only of pixel data having a Doppler datum lying in a predetermined range;

(b) retrieving a source set of the pixel data from said memory, the pixels included in said source pixel data set being a function of the pixels included in said reference pixel data set; and (c) volumetrically rendering the intensity data in said source pixel data set by projecting onto an image plane, thereby forming a volume projected data set representing a projected image; and a display device for displaying said projected image.

22. The imaging system as defined in claim 21, wherein said Doppler data comprises velocity data.

23. The imaging system as defined in claim 21, wherein said Doppler data comprises power data.

24. An imaging system comprising:

an ultrasound transducer array comprising a multiplicity of transducer elements;

a transmit beamformer coupled to said transducer array in a transmit mode;

a receive beamformer coupled to said transducer array in a receive mode;

a computer programmed to perform the steps of:

(a) controlling said transmit beamformer in said transmit mode to cause said transducer array to transmit a plurality of beams in sequence;

(b) controlling said receive beamformer in said receive mode to form respective beamsummed receive signals from respective sets of signals transduced by said transducer array following transmission of said respective beams;

(c) deriving respective sets of Doppler data from said beamsummed receive signals;

(d) deriving respective sets of intensity data from said beamsummed receive signals;

(e) storing said sets of Doppler and intensity data in the form of sets of pixel data, each pixel datum comprising a Doppler datum and an intensity datum derived from ultrasound scattered from a particular sample volume;

(f) determining a reference set of said stored pixel data, said reference pixel data set consisting only of pixel data having a Doppler datum lying in a predetermined range;

(g) retrieving a source set of the pixel data from said memory, the pixels included in said source pixel data set being a function of the pixels included in said reference pixel data set; and (h) volumetrically rendering the intensity data in said source pixel data set by projecting onto an image plane, thereby forming a volume projected data set representing a projected image; and a display device for displaying said projected image.

25. The imaging system as defined in claim 24, wherein said Doppler data comprises velocity data.

26. The imaging system as defined in claim 24, wherein said Doppler data comprises power data.

* * * * *